(12) United States Patent
Weitzel et al.

(10) Patent No.: US 11,344,254 B2
(45) Date of Patent: May 31, 2022

(54) ESTIMATING HYDRATION USING CAPILLARY REFILL TIME

(71) Applicant: Welch Allyn, Inc., Skaneateles Falls, NY (US)

(72) Inventors: Richard Howard Weitzel, Aloha, OR (US); Steven D. Baker, Beaverton, OR (US); Richard Allen Sunderland, Clive, IA (US); Matthew Lee Hansen, Portland, OR (US); David Clark Sheridan, Beaverton, OR (US)

(73) Assignees: Welch Allyn, Inc., Skaneateles Falls, NY (US); Oregon Health & Science University, Portland, OR (US)

( * ) Notice: Subject to any disclaimer, the term of this patent is extended or adjusted under 35 U.S.C. 154(b) by 817 days.

(21) Appl. No.: 15/405,412

(22) Filed: Jan. 13, 2017

(65) Prior Publication Data

US 2017/0209091 A1    Jul. 27, 2017

Related U.S. Application Data

(60) Provisional application No. 62/286,043, filed on Jan. 22, 2016, provisional application No. 62/324,941, filed on Apr. 20, 2016.

(51) Int. Cl.
*A61B 5/00* (2006.01)
*A61B 5/01* (2006.01)
*A61B 5/024* (2006.01)

(52) U.S. Cl.
CPC .......... *A61B 5/4875* (2013.01); *A61B 5/0053* (2013.01); *A61B 5/0059* (2013.01);
(Continued)

(58) Field of Classification Search
CPC ... A61B 5/4875; A61B 5/0053; A61B 5/7278; A61B 5/6826; A61B 5/6829; A61B 5/01;
(Continued)

(56) References Cited

U.S. PATENT DOCUMENTS 8,082,017 B2  12/2011  Messerges et al.
8,610,769 B2  12/2013  Buxton et al.
(Continued)

FOREIGN PATENT DOCUMENTS

CN  104207788 A  12/2014
CN  107106051 A   8/2017
(Continued)

OTHER PUBLICATIONS

Definition of clinical. Merriam-Webster Dictionary, retrieved on Apr. 4, 2021; Retrieved from the Internet <https://www.merriam-webster.com/dictionary/clinical (Year: 2021).*
(Continued)

Primary Examiner — Gary Jackson
Assistant Examiner — Sebastian X Lukjan
(74) Attorney, Agent, or Firm — Merchant & Gould P.C.

(57) ABSTRACT

An example system for estimating a hydration level of an individual can include: a mechanism configured to apply mechanical pressure to a digit of the individual; an light detector configured to sense the light from the digit; and a controller programmed to perform functions including: send a first signal to the mechanism to apply the mechanical pressure to the digit; send a second signal to the mechanism to release the mechanical pressure on the digit; determine a capillary refill time based upon a third signal from the light detector indicating an amount of time for capillaries of the individual to refill with blood; and estimate the hydration level of the individual based upon the capillary refill time and one or more additional parameters.

20 Claims, 4 Drawing Sheets

(52) U.S. Cl.
CPC ............ *A61B 5/01* (2013.01); *A61B 5/02422* (2013.01); *A61B 5/6826* (2013.01); *A61B 5/6829* (2013.01); *A61B 5/7278* (2013.01); *A61B 5/742* (2013.01); *A61B 5/746* (2013.01)

(58) Field of Classification Search
CPC ..... A61B 5/02422; A61B 5/742; A61B 5/746; A61B 5/0059; A61B 5/0082
See application file for complete search history.

(56) References Cited

U.S. PATENT DOCUMENTS

| | | | |
|---|---|---|---|
| 8,641,613 B2 | 2/2014 | Coelho | |
| 8,641,614 B2 | 2/2014 | Coelho | |
| 8,727,980 B2 | 5/2014 | Coelho | |
| 8,747,328 B2 | 6/2014 | Tichauer | |
| 8,758,259 B2 | 6/2014 | Suzuki | |
| 8,989,832 B2 | 3/2015 | Debreczeny et al. | |
| 9,848,787 B2 | 12/2017 | White et al. | |
| 10,154,817 B2 | 12/2018 | Whitfield | |
| 2007/0282182 A1 | 12/2007 | Messerges et al. | |
| 2009/0105556 A1 | 4/2009 | Fricke | |
| 2009/0143655 A1* | 6/2009 | Shani | A61B 5/0059 600/323 |
| 2013/0018241 A1* | 1/2013 | Bezzerides | A61B 5/14552 600/324 |
| 2013/0317322 A1* | 11/2013 | Andrijauskas | A61B 5/14546 600/309 |
| 2014/0148658 A1* | 5/2014 | Zalevsky | A61B 3/102 600/301 |
| 2015/0112169 A1 | 4/2015 | Lamego et al. | |
| 2015/0342468 A1 | 12/2015 | Semler et al. | |
| 2016/0038043 A1* | 2/2016 | Mulligan | A61B 5/4848 600/301 |
| 2018/0263558 A1 | 9/2018 | Cronin et al. | |
| 2021/0186371 A1 | 6/2021 | Siu et al. | |
| 2021/0369124 A1 | 12/2021 | Sheridan et al. | |

FOREIGN PATENT DOCUMENTS

| | | | |
|---|---|---|---|
| EP | 3 028 630 A2 | 6/2016 | |
| JP | 6-28662 B2 | 4/1994 | |
| JP | 2012-115640 A | 6/2012 | |
| JP | 2018-108278 A | 7/2018 | |
| JP | 6626915 B2 | 12/2019 | |
| JP | 6665282 B2 | 3/2020 | |
| KR | 10-2011-0080372 A | 7/2011 | |
| KR | 10-1459652 B1 | 11/2014 | |
| RU | 2015 138 778 A | 3/2017 | |
| WO | WO-2009053920 A1 * | 4/2009 | ........... A61B 5/0059 |
| WO | 2013/049837 A1 | 4/2013 | |
| WO | WO-2015085240 A1 * | 6/2015 | ............. A61B 5/441 |
| WO | WO-2015155526 A1 * | 10/2015 | |
| WO | WO-2016077765 A1 * | 5/2016 | ........... A61B 5/7257 |
| WO | WO-2016097979 A1 * | 6/2016 | ........... A61B 5/6898 |
| WO | 2021243078 A1 | 12/2021 | |

OTHER PUBLICATIONS

Shamsudin, Nebil Muaied, A device for measurement of capillary refilling time, 2012, 67 pages.

Alpert et al., "Oscillometric blood pressure: a review for clinicians," Journal of the American Society of Hypertension, vol. 8, Iss 12, Dec. 2014, pp. 930-938.

Vandenberk et al., "Clinical Validation of Heart Rate Apps: Mixed-Methods Evaluation Study," JMIR Mhealth Uhealth, vol. 5, Iss 8, e129, doi:10.2196/mheath.7254, 15 pages (2017).

* cited by examiner

ESTIMATING HYDRATION USING CAPILLARY REFILL TIME

BACKGROUND

Pediatric dehydration is a common complaint. For example, the most common complication of children with viral illness is dehydration. Caregivers need to assess the degree of dehydration in order to determine which children may benefit from various interventions, such as hospitalization and/or intravenous fluid hydration. Current methods of dehydration assessment, such as a parent report of urine output and oral intake, or weight prior to illness, have been shown to be inaccurate due to their subjective nature. Lab blood tests are more accurate, but such tests are expensive, time consuming and typically provided only for children who are at least moderately dehydrated.

SUMMARY

In general terms, this disclosure is directed to systems and methods for estimating hydration using capillary refill time. Various aspects are described in this disclosure, which include, but are not limited to, the following aspects.

DETAILED DESCRIPTION

Various embodiments will be described in detail with reference to the drawings, wherein like reference numerals represent like parts and assemblies throughout the several views.

The example systems and methods described herein are generally related to estimating hydration using capillary refill time.

As described in more detail below, such a system can include a medical device having a pressure system for applying mechanical pressure to a portion of an individual, such as the individual's fingertip, to remove a volume of blood from the capillary bed, and a sensing system to estimate the refill time for capillary bed of that individual. Using the capillary refill time, along with other possible physiological and/or ambient information, the medical device can provide an objective estimate of a hydration level of the individual.

The medical device may include a contoured surface to match the shape of the digit (finger or toe), or other body part such as the chest, back, heel, sacral area, trochanter, etc. The contour helps decrease motion artifact. The system may lock around a digit to decrease motion artifact and it may move with the digit. Locking may be achieved using Velcro, adhesive or similar method.

The system may be very small so that it easily moves with the digit so as to reduce motion artifact.

The entire sensor system and analysis may be completed within a single, patient-worn module. This module could have data connections and allow automated measurements of capillary refill times (CRT) that are either stored locally or uploaded to a computing device such as a PC, patient monitor, smart phone. Such an automated system may be desirable to detect recovery from dehydration or to verify continued perfusion in a patient who has had vascular surgery on an extremity. Data connections may be via radio such as cellular, WiFi, Bluetooth, ZigBee, ANT, NFC or other physical layer. The data connection may be over a wired solution such as USB, CAN bus, Ethernet, RS-232 or other physical layer.

The system may be powered via the communication, such as power over Ethernet, USB, NFC. The system may be powered by a battery, wireless power, for example, Qi, or energy harvesting. Energy harvesting may, for example, be adequate when the system has a manual method to blanch the capillary bed and the system must only support detection of the CRT. In the manual system, a clinician may blanch the nailbed as is typically done in a patient exam, and the system provides accurate measurement of the capillary refill time. The clinician may also blanch the nailbed using a circumferential cuff inflated using a squeeze bulb or by pressing a plunger that is located over the skin area to be blanched. The manual system may support timing, pressure, and/or annunciators to guide the clinician to provide the pressure for the proper amount of time and intensity. Such a system may also include temperature system as described below.

The system may make a determination of acceptable or unacceptable data and prompt the clinician for another measurement. Automated systems may automatically make another measurement. The system may provide a real-time indicate of acceptable signal to guide the patient and/or clinician to provide proper positioning, decrease motion, or the like.

The sensor system may be disposable. In such an example, the sensor system is configured for a single use on a patient. Once used, the sensor system can be disposed of or recycled for further use. In another example, the sensor system can be a multi-use system. In that example, the sensor system can be used multiple times on a single patient or on multiple patients. The sensor system can be configured to be sterilized or otherwise cleaned between uses. Other configurations are possible.

The medical device may operate using either a single or multiple light sources. It may use single or multiple optical detectors. The light sources and detectors may be disposed in a single miniature package and may be hermetically sealed to protect the sensor and support cleaning. The detector may have one or more of the following: an amplifier to improve the signal-to-noise ratio (SNR), a filter to remove unwanted signals, and an analog-to-digital converter (ADC) to digitize the signals. The amplifier, filter and ADC may be co-located with the detector to further improve the SNR. A single package may contain the amplifier, filter, and ADC converter. The ADC converter may be designed to have sufficient dynamic range to allow detection of small signals while not saturating, for example, using a 24-bit ADC. The system may be designed to detect and subtract ambient light at using either the analog or digital methods. For example, detecting the ADC output when no LEDs are illuminated provides a measure of the ambient light level.

The system may use a circumferential compression to blanch the nailbed of a finger or toe. Circumferential pressure may more fully blanch the nailbed with less pressure than point contact methods and adds the feature of locking the detector and light source against the skin. Further, circumferential pressure inherently blocks ambient light. The circumferential compression may be actuated using air, magnetics, or electrical drive. For example, an annular air bladder may be inflated or a motor with a worm drive may be used, similar to a hose clamp. The circumferential compression may have an external wall that is stiff so that only the internal diameter decreases when a bladder is inflated. The system may include a pressure detector to determine how much pressure has been applied and for what duration. The pressure detector may be instantiated using NEMS or MEMS technology, a strain gage, piezo element, or similar detector.

The system may support detecting capillary refill times when the finger is covered to prevent spread of disease and reduce the need for cleaning and sanitizing the sensor, for example, using a finger cot.

The medical device may be calibrated to match the capillary refill times as determined by clinicians. For example, for each set of CR waveforms the system measures, multiple clinical reviews of the patient's CRT may be made and these clinical reviews are used to train the algorithms that interpret the waveform to determine a CRT. Similarly, the system may be calibrated to match actual clinical dehydration. For example, for each set of CR waveforms the system measures, a percent dehydration is computed from dehydrated and rehydrated weight. The percent dehydration along with the CR waveforms from many patients are used to train the algorithms that interpret the waveform to determine a percent dehydration.

The system may be calibrated to match actual clinical dehydration across a range of digit temperatures. For example, for each set of CR waveforms the system measures a fingertip temperature is also measured and recorded. From the patient's dehydrated and rehydrated weight, a percent dehydration is calculated. The percent dehydration, fingertip temperature and the CR waveforms for many patients are used to train the algorithms that interpret the waveform to determine a percent dehydration as a function of both the waveform morphology and the digit temperature.

The system may be trained for other determinations such as a patient with a high likelihood of developing sepsis or bed sores. The output of the sensor may be used with other measures to determine if a patient is developing or recovering from disease.

Skin temperature may be determined using sensors include a thermistor, a thermocouple, or a semiconductor such as a diode. The skin temperature may be detected using a system that includes amplification and/or filtering and/or digitization next to the temperature sensor to improve the signal-to-noise ratio. The skin temperature measure may be improved through use of thermally conductive material in contact with the sensor and/or thermally insulate material to shield the temperature sensor from external sources.

As used herein, the term "caregiver" can include a doctor, nurse, certified nursing assistant, physician assistant, and/or other practitioners that provide healthcare services. In addition, the caregiver can be a parent, guardian, or other individual that may supervise another individual's health.

The term "individual" and "patient" are used interchangeably herein to mean a human that receives health care services from a caregiver. The patient can be a child or adolescent. The patient can also be an adult.

Figure 1:
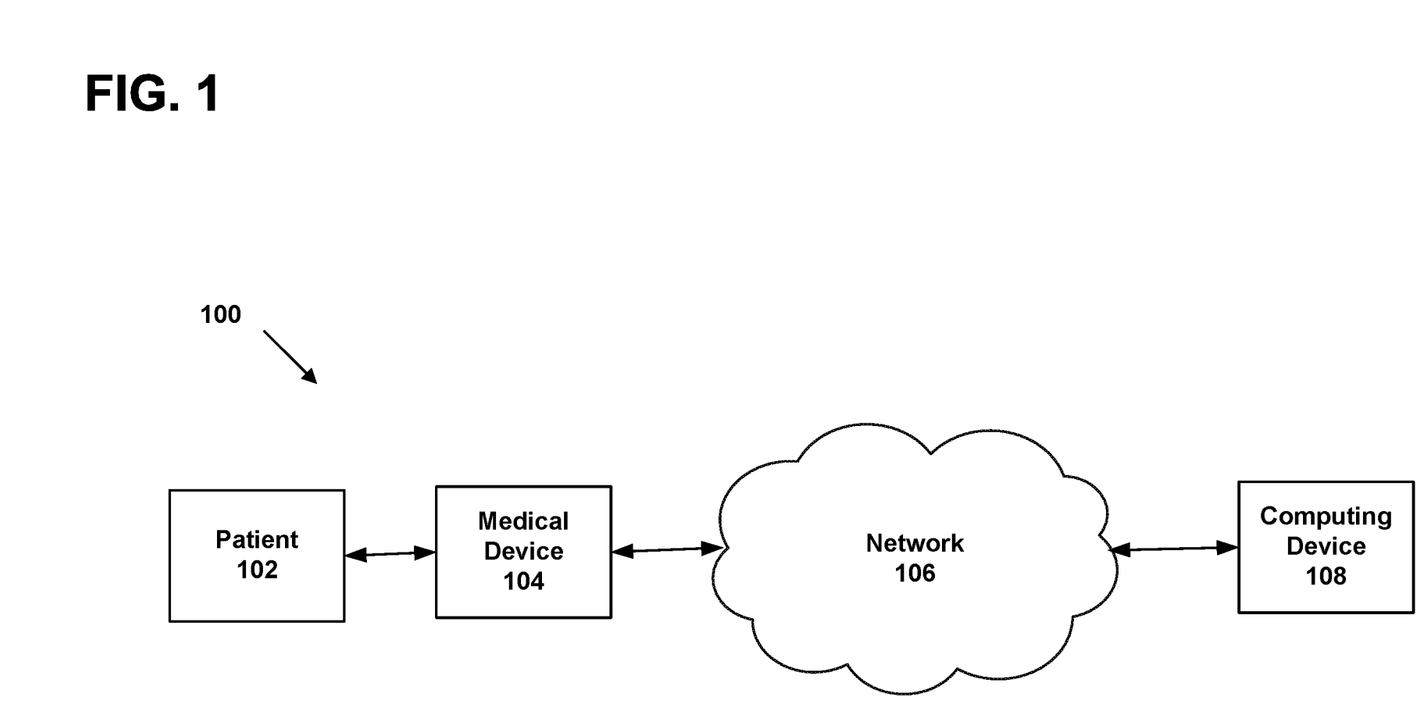
FIG. 1 shows an example system for estimating hydration using capillary refill time.

Referring now to FIG. 1, an example system 100 is shown for estimating hydration using capillary refill time. In this example, a medical device 104 is configured to estimate the capillary refill time for a patient 102. The capillary refill time is used, in turn, to estimate a hydration level of the patient 102.

The estimation of hydration of the patient can be used by a caregiver to determine if an intervention, such as a hydration therapy like intravenous fluids, is necessary. The capillary refill time and/or estimate of hydration, in some embodiments, can be communicated through a network 106, such as the Internet, to a computing device 108 for analysis and/or storage, such as in an electronic medical record associated with the patient 102. Computing device 108 may be a patient monitor, smart phone, table, PC or other computing device. The computing device 108 can also be a server capable of running a server application. In some embodiments, the computing device 108 can be directly connected to the medical device 104 without traversing a network connection.

Figure 2:
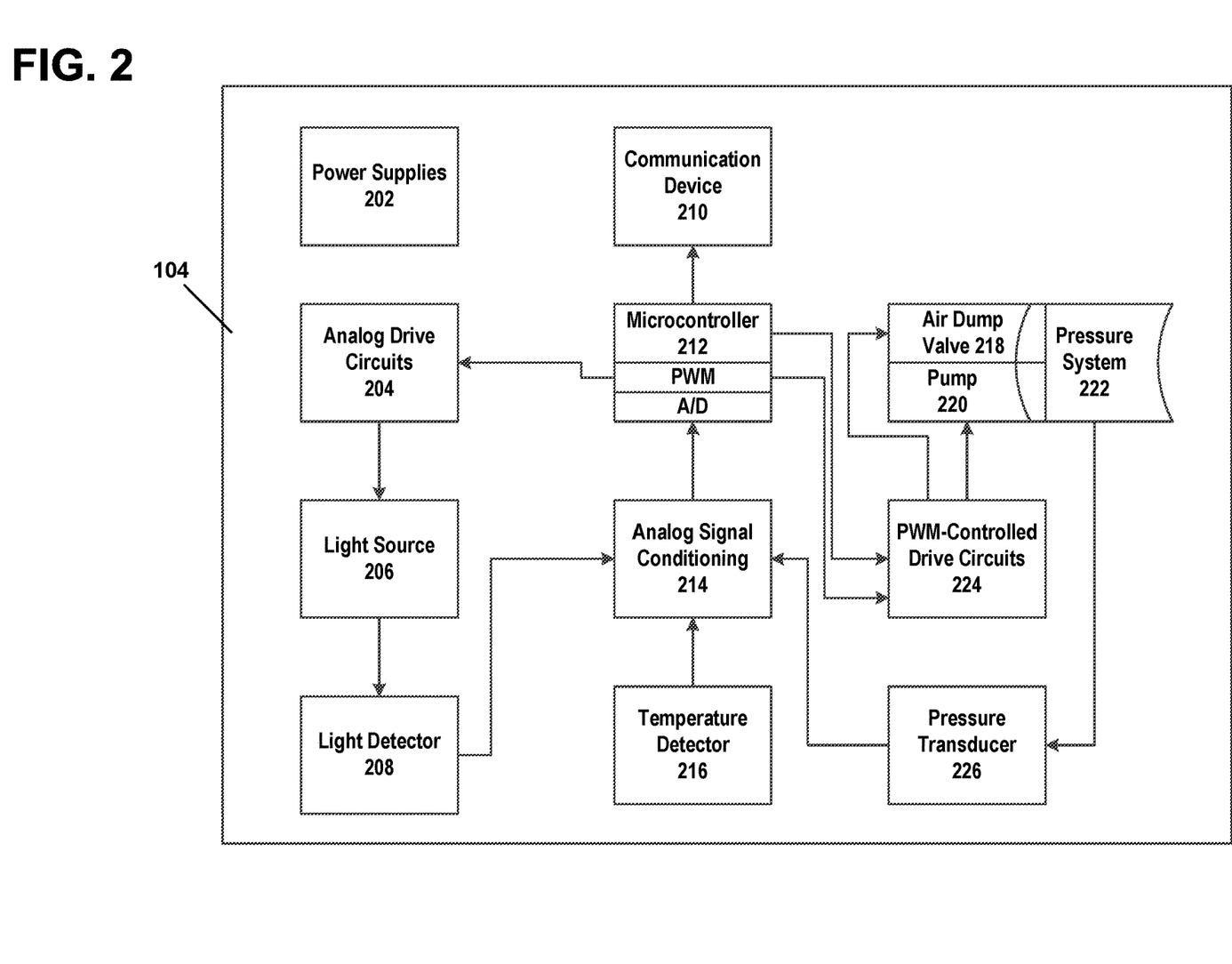
FIG. 2 shows an example device from the system of FIG. 1 for estimating hydration using capillary refill time.

Referring now to FIG. 2, additional details about the example medical device 104 are provided.

In general, the medical device 104 is configured to apply mechanical pressure to a portion of the body of the patient 102. In this example, the portion is a digit, such as a finger (phalange) of the patient. In other embodiments, other locations upon the patient's body can be used, such as the patient's arm, torso, or toe. The pressure is applied to void blood from the patient's capillary bed and held for a short period of time. Thereupon the pressure is released.

The medical device 104 is further configured to using an optical sensor to estimate a refill time for the patient's capillary bed once the mechanical pressure is released. The optical sensor measures an intensity of light from a light source (either passed through or reflected from the patient's tissues and blood) and allows the medical device 104 to estimate how long it takes for the capillary bed to refill with blood. The light source may be ambient light.

Finally, based on the capillary refill time (and possibly other factors such as the ambient environment), the medical device 104 is configured to provide an estimate of the hydration level of the patient 102.

As shown in FIG. 2, the medical device 104 includes one or more power supplies 202 configured to provide power to the medical device 104. In this example, the power is low voltage, such as being regulated power at 3.3 and 5 volts as needed by the various components of the medical device 104, as described below. In some examples, the medical device 104 can be powered using a mains power source or can be powered using a battery.

The medical device 104 includes analog drive circuits 204 that provide sufficient power (as controlled by a microcontroller 212) to drive the various analog circuits of the medical device 104.

A light source 206 of the medical device 104 shines light into the skin of the patient 102. The light from the light source 206, which is typically a light emitting diode (LED) that may be tuned to emit at various wavelengths, is reflected back (or transmitted through the finger) and received by a light detector 208. In other embodiments, other types of light, such as white, ultraviolet and/or infrared light, can be used.

The light detector 208 of the medical device 104 senses light that is passed through or reflected by the tissue and blood in the capillaries of the fingertip of the patient 102. In example embodiments, the light detector 208 is a photodetector such as a photodiode or similar device. The light detector 208 can detect fluctuations in the amount of (i.e., intensity of) light that is passed through or reflected based upon the amount of blood in the capillaries at a given point in time. These light intensities vary as the capillaries fill and empty of blood.

The medical device 104 uses the light source 206 to sense the differences in intensity of the light indicative of the heart beat pulse and the filling of the capillary bed of the patient with blood to allow for an estimate of the capillary refill time, as described more below. Preferably the light detector 208 is configured to exclude ambient light.

Various configurations can be used to determine the intensity of light. In one configuration, an intensity of light that is transmitted through the finger is measured. In another configuration, an intensity of light that is reflected from the fingertip is detected. In either scenario, an LED light source is used at a specific single wavelength band, typically characterized by the wavelength at the center of the band. Detectors that can be used in this scenario include phototransistor, photomultiplier, photomultiplier tube, CMOS imager, CCD imager, and photodiode. Cameras such as CCD and CMOS imagers can be used. Such a camera may be a boresight camera. The LED light source may use long wavelengths such as red or infrared light or use short wavelengths such are green, blue, and violet. Green light, for example in the 495-570 nm wavelength band may be used as this color has been shown to have better signal-to-noise ratio for AC components during the presence of motion artifact and to have strong sensitivity to low perfusion.

In some examples, multiple light sources from differing angles can be used to improve the light intensity measurements. Likewise, multiple light detectors can be used, including detection of transmitted as well as reflected light.

The microcontroller 212 of the medical device 104 controls various components of the medical device, such as the light source 206 and a pump 220 using a pulse width modulated (PWM) output and records the data from components like a temperature detector 216, light detector 208, pump 220, and pressure transducer 226. PWM control of the pump 220 and light source 206 allow for precise control over the pump rate and brightness, respectively. Other embodiments may use other features of a microcontroller such as a Digital-to-Analog Converter (DAC) to control external components such the pump and LED brightness. The microcontroller 212 is also programmed, in some embodiments, to analyze the outputs of these components and to provide an estimate of a hydration level of the patient.

The microcontroller 212 interfaces with a communication device 210 that allows the medical device 104 to communicate with one or more other devices, such as the computing device 108 through the network 106, using various protocols, such as Bluetooth or Wi-Fi. The communication device may also be a wired connection, such as Ethernet, USB, RS-232 and the like.

An analog signal conditioning module 214 of the medical device 104 provides gain, offset, and filtering to the raw signals from the various components of the medical device 104 to provide a signal appropriate for the analog to digital convertor (A/D) of the microcontroller 212. For example, the analog signal conditioning module 214 can condition signals from the light detector 208, temperature detector 216, and pressure transducer 226.

The temperature detector 216 provides a measure of the temperature of the finger-tip of the patient 102. As noted, various factors, such as temperature, can impact the capillary refill rate independent of the patient's hydration status. The microcontroller 212 can use the temperature measurement from the temperature detector 216 when estimating the hydration level of the patient 102. In some examples, the temperature detector 216 can be a thermocouple or thermistor positioned to touch the fingertip and measure the temperature thereof. In other examples, other temperature sensing devices can be used, such as an infrared temperature detection sensor.

The temperature detector 216 can also be configured to measure an ambient temperature of the environment. This can be done using one or more of the technologies described above.

In some examples, the temperature detector 216 can also be used, for example, to sense other factors, such as the presence or absence of the patient's fingertip. This may be used to determine when to power light source 206. Alternately, light source 206 may be powered and finger insertion may be detected when the detected light level changes.

A pressure system 222 of the medical device 104 includes an air dump valve 218 and the pump 220. A PWM-controller drive circuit 224 of the medical device 104 is used to control the pressure system 222. Specifically, the pump 220 is driven to provide mechanical pressure to the patient's finger. In this example, the fingertip is blanched, i.e., pressure is applied to remove a volume of blood in the capillary bed of the finger. Manual application of pressure may also be used. For manually-applied pressure, the system might provide an indicator of the pressure and/or an indication when an appropriate target pressure, e.g., 100 mmHg is achieved. The system may use the patient's age, weight and/or blood pressure as in input to determine the appropriate target pressure. For example, a neonatal patient may have a target pressure of 80 mmHg, while an adult may have a target pressure of 180 mmHg and a pediatric patient between 1 month and 17 years may have a target pressure of 100 mmHg. The system may analyze the pressure and/or optical waveforms to determine when to stop increasing the pressure. For example, the knee in the curve shown in FIG. 4 annotated "stop applying pressure."

In some examples, the pressure system 222 can generally be shaped to match the contours of the finger. For example, the pump 220 can include a structure that captures the fingertip and a linear motor that moves the pump 220 to apply pressure to the finger. In other examples, other configurations can be used to apply pressure. For example, in another embodiment, a cuff (similar to that of a blood pressure cuff) can be positioned around the finger and inflated to provide the mechanical pressure.

At a desired time, the mechanical pressure is relieved by actuating the air dump valve 218 that releases the pressure. In the examples provided above, the air dump valve 218 can simply include reversal of the linear motor and/or a release of the pressure of the air in the inflated cuff. Release of the pressure may be done manually, with the microcontroller indicating when the manual release should occur or with external timing. At that time, the refill time for the capillary bed can be measured using the intensity of light sensed by the light detector 208. The output of light detector 208 that changes as pressure is increased may be used to determine when sufficient pressure has been applied to blanch the nail bed.

The pressure transducer 226 measures the pressure applied to the patient's fingertip by the pump 220 and is used along with the output from the light detector 208 to verify pressure is high enough to create blanching of the nail bed (i.e., remove a sufficient volume of blood from the capillary bed so that the refill time can be estimated). In some examples, the pressure transducer 226 can be a strain gauge. Other configurations are possible.

Figure 3:
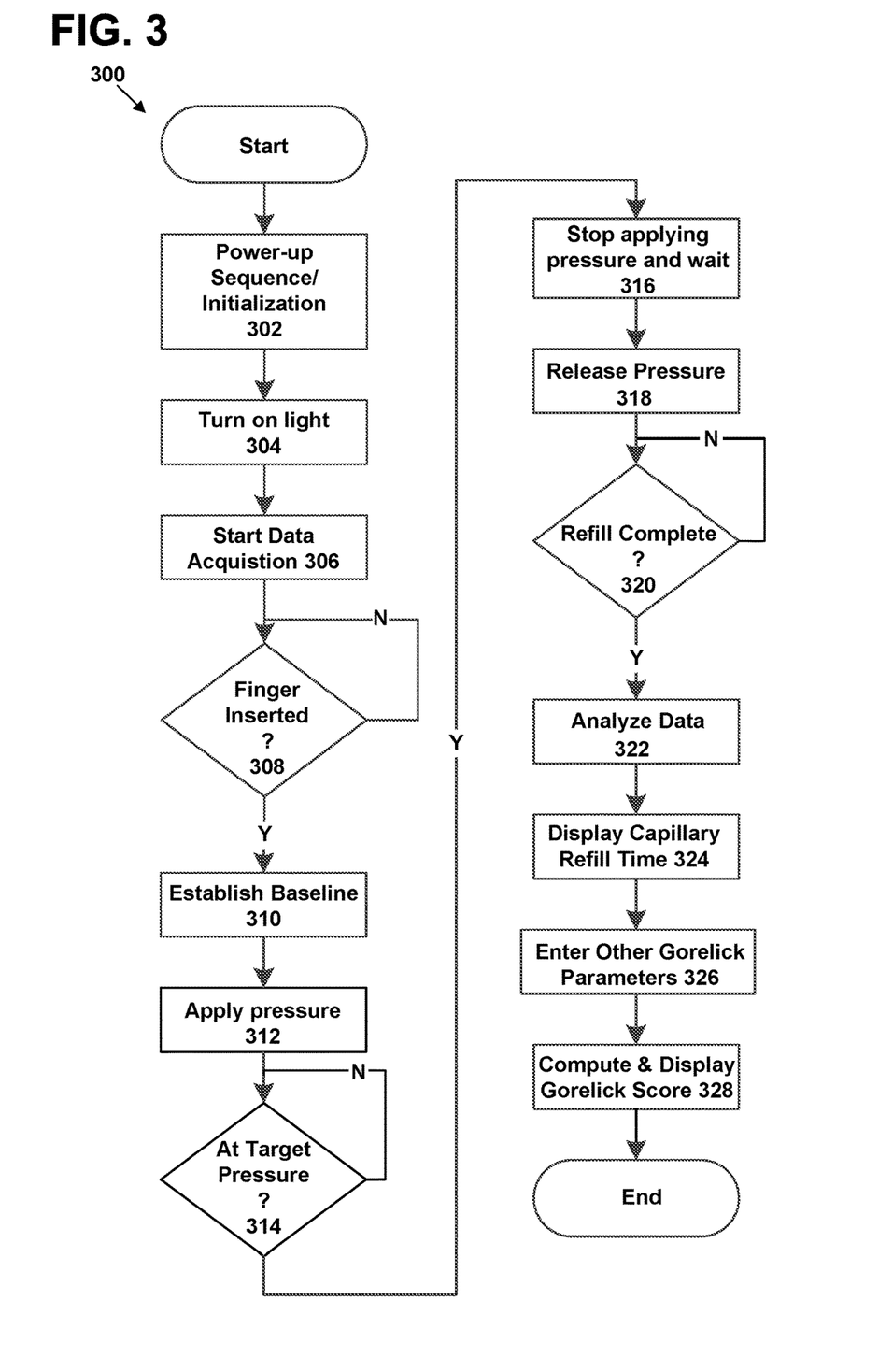
FIG. 3 shows an example method for estimating hydration using capillary refill time.

Referring now to FIG. 3, an example method 300 for the medical device 104 to estimate a hydration level of the patient is depicted. Many of the operations of the method 300 are accomplished by the microcontroller in conjunction with one or more other components of the medical device.

At operation 302, the medical device is powered up and initialized. During this operation, one or more initialization processes can be done, such as testing of the pump, and other components of the medical device to assure proper functioning.

Next, at operation 304, the light source is activated and data acquisition is started at operation 306. At operation 308, a determination is made regarding whether or not the patient's finger is present. If not, the medical device continues to wait for the patient's fingertip to be inserted into the medical device. As mentioned above, other methods, such as temperature may be used to determine when the finger is inserted and thereafter turning on the light at operation 304.

Once the medical device determines the finger is present, control is passed to operation 310, and the light detector determines a baseline for the intensity of light that is either passed through or reflected from the patient's finger.

Next, at operation 312, mechanical pressure is applied to the fingertip to blanch the finger. At operation 314, a signal from the pressure transducer is used to determine if the applied pressure is at the desired amount. If not, additional pressure is applied. The pressure can be applied automatically or under the control of the caregiver.

If so, control is passed to operation 316, and the mechanical pressure is maintained at the desired level. An optional step (not shown) of measuring the fingertip temperature may be made at this time. At the desired time (see additional explanation below), the mechanical pressure is released at operation 318. The release can be automated or under the control of the caregiver.

The light detector is used at operation 320 to measure the light intensities as the capillary bed refills. Next, at operation 322, the microcontroller analyzes the light intensity data (see FIG. 4) to estimate the capillary refill time.

Figure 4:
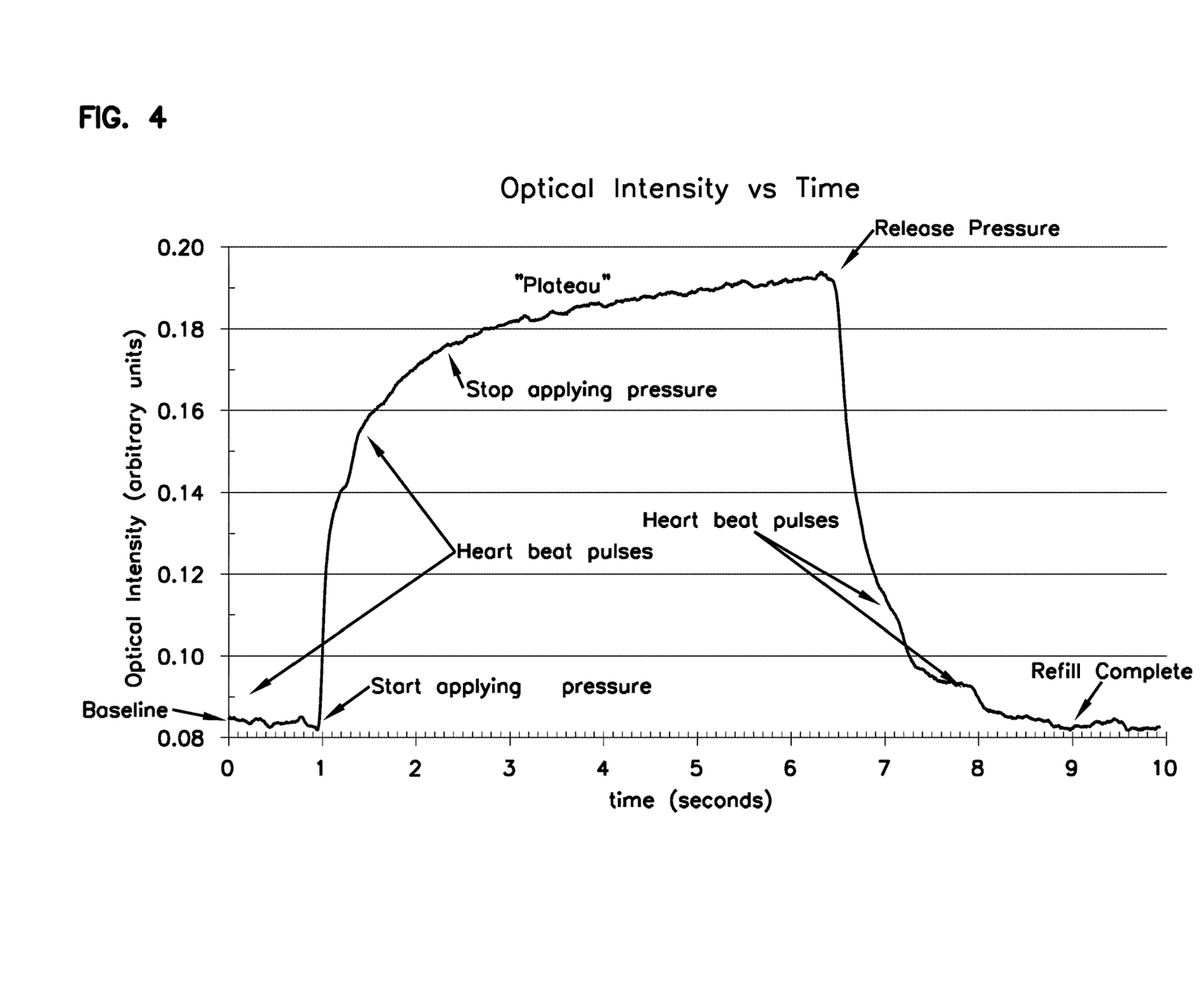
FIG. 4 shows an example curve illustrating optical intensity measured from a capillary bed of an individual.

For example, referring to FIG. 4, an example plot 400 illustrating the optical intensity of light measured from a capillary bed of the patient is shown. Time (in seconds) is shown on the X-axis, and the optical intensity (in arbitrary units) is shown on the Y-axis. As pressure is applied at approximately one second, the light intensity curve rises until a general plateau is reached at approximately 6.5 seconds. In some examples, the medical device determines a slope of the curve and automatically sets a pressure as the slope approaches zero (or is substantially flat). At that time, the pressure is released and the light intensity curve drops rapidly towards the baseline. The time between the release of the pressure (~6.5 seconds) and the return to baseline (i.e., approximately 9 seconds) is an approximation of the capillary refill.

The plot 400 also illustrates various pulse rate pulses that are captured during the process. These heart beat pulses can be used to determine an amount of pressure to apply and/or to determine when refill is complete. For example, the medical device 104 can estimate an amplitude of the heart beat pulses and then use a specified ratio to determine an amount of pressure to apply before capillary refill is measured. In another example, the medical device 104 waits until a specified heart beat pulse or heart beat pulse amplitude is sensed to determine that capillary refill is complete. Other methods of determining the amount of pressure to apply, such as age-based lookup tables, using the patient's blood pressure, or analyzing other aspects of the optical intensity curve such as the slope, may be used.

In example embodiments, the capillary refill time may be determined from various aspects of the waveform, such as the slope of the optical signal at various points in the curve (slope changes over time), the time constant of the optical signal, the time for the optical signal to return to baseline optical intensity, ratios of durations or amplitudes of various sections of the curve or a combination thereof.

Further, the estimate of the capillary refill time can be modified based upon other factors, such as temperature. For example, fingertip temperature, core temperature, and/or ambient temperature can be used to either validate and/or modify the estimate of capillary refill time and/or to modify the estimate of dehydration. For example, a patient with a normal hydration and fingertip temperature of approximately 33 degrees Celsius may have a 500 millisecond capillary refill time. The same patient with a typical fingertip temperature of approximately 30 degrees Celsius may have a 2.5 second capillary refill time. While the measured capillary refill times differ substantially, the system could indicate that the equivalent capillary refill time for a patient with warm (typical temperature) fingers would be in a range of 0.4 to 0.7 seconds with a 95% confidence interval.

The medical device can optionally display the capillary refill time to the caregiver and/or patient at operation 324. In such an example, the medical device can include a graphical user interface and one or more input/output devices that allow for the display of various parameters and input of parameters to the medical device. In other examples as described further below, the data collected by the medical device may instead be communicated to another device, such as the computing device 108, for analysis, storage (e.g., in the EMR), and presentation to the caregiver.

Referring again to FIG. 3, next, at operation 326, other parameters associated with estimating the hydration level of the patient are collected. In some examples, these other parameters are automatically captured by the medical device, such as quality of pulse rate pulses and pulse rate. In other examples, the other parameters can be manually entered by the caregiver and/or patient, such as: general appearance; presence of tears; appearance of mucous membranes; appearance of eyes; breathing; skin elasticity; and urine output.

Finally, at operation 328, an estimate of the hydration level of the patient is computed and optionally displayed. In this example, a specific methodology, such as the Gorelick Score, is used to estimate the hydration level. The Gorelick Score is presented as part of the Gorelick Scale, which is a 10-point or 4-point scale using some or all of the automatic and manual parameters noted above to estimate a hydration level of the patient.

Other methods of estimating hydration level can also be used. This includes, for example, combining the capillary refill time with one or more other scales, such as the WHO scale (using condition, eyes, thirst, and skin feel as other parameters) and/or the Clinical Dehydration Scale (using general appearance, appearance of eyes, appearance of mucous membranes, and presence of tears).

In yet other examples, the medical device 104 is programmed to take multiple reading of the capillary refill time and to average those readings. In that manner, the signal to noise ratio can be increased and outliers may be rejected.

As described above, the medical device 104 can include a display to show the capillary refill time and/or the estimate of the hydration level. The hydration level can be presented according to a scale (such as the Gorelick Scale described above). Alternatively, other methods of presentation can be used. For example, the medical device can simply provide an alert (e.g., display a warning or light an LED) if the hydration level is estimated to be at a point (e.g., exceed a threshold) at which action should be taken. Alerts can be automatically generated and sent to the caregiver in such a scenario. Many alternatives are possible, including messages that are appropriate to parents or other caregivers that are consistent with the rehydration therapy required for that patient. For example, a moderately dehydrated patient may be given small amounts of liquid to drink while a severely dehydrated patient preferably receives IV fluids because of the high likelihood ingesting fluids will cause vomiting.

As noted, the medical device 104 can be programmed to calculate the estimation of the capillary refill time and/or the hydration level. In other embodiments, one or both of these values can be calculated by another device, such as the computing device 108. In such an embodiment, the parameters gathered by the medical device (both automatically and manually) can be sent to a computing device, such as a central server. The central server can calculate the estimation of hydration and send that estimate to the caregiver and/or patient. The values can also be stored in the patient's EMR.

In the example shown, the medical device 104 is a standalone device that is configured to estimate the capillary refill time and hydration level. In this example, the medical device can include a housing and provide an aperture into which the patient places his/her finger. The aperture may change size to match the diameter of the inserted digit as a means of securing the sensor to the digit and/or to reduce motion artifact. The mechanical pressure can be provided by various mechanisms provided within the housing, such as a clamp or other device.

In another embodiment, the medical device can include a separate tether that is applied to a patient's fingertip, similar to that of a fingertip temperature sensor and/or SPO2 sensor. In this scenario, the fingertip sensor incorporates the light source and detector, temperature sensor, pressure transducer, and mechanical components necessary to provide the pressure. The tether can be coupled to the medical device using wired and/or wireless techniques.

In yet another embodiment, components of the medical device 104 can be incorporated into other devices. For example, the mechanical device can be incorporated into an SPO2 sensor, so that the light source and detector, temperature sensor, pressure transducer, and the mechanical components necessary to provide the pressure are incorporated as part of the SPO2 sensor that is applied to the fingertip of the patient. Many alternative configurations are possible.

In example embodiments, the medical device 104 is a computing device that executes an operating system, application programs, and software modules (including the software engines) described herein. The medical device 104 can be a computing device of various types. In some embodiments, the medical device 104 is a mobile computing device. Examples of the medical device 104 as a mobile computing device include a mobile device (e.g., a smart phone and a tablet computer), a wearable computer (e.g., a smartwatch and a head-mounted display), a personal digital assistant (PDA), a handheld game console, a portable media player, an ultra-mobile PC, a digital still camera, a digital video camera, and other mobile devices. In other embodiments, the medical device 104 is other computing devices, such as a desktop computer, a laptop computer, or other devices configured to process digital instructions.

It is recognized that the architecture of medical device 104 can also be implemented in other computing devices used to achieve aspects of the present disclosure. For example, the computing device 108 can be configured similarly to that of the medical device 104.

The medical device 104 includes, in some embodiments, at least one processing device, such as a central processing unit (CPU) or the microcontroller 212. A variety of processing devices are available from a variety of manufacturers, for example, Intel or Advanced Micro Devices. In this example, the medical device 104 also includes a system memory, and a system bus that couples various system components including the system memory to the processing device. The system memory includes read only memory and random access memory. A basic input/output system containing the basic routines that act to transfer information within the medical device 104, such as during start up, is typically stored in the read only memory.

The medical device 104 also includes a secondary storage device in some embodiments, such as a hard disk drive, for storing digital data. The secondary storage device is connected to the system bus. The secondary storage devices and their associated computer readable media provide nonvolatile storage of computer readable instructions (including application programs and program modules), data structures, and other data for the medical device 104.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device or memory, including an operating system, one or more application programs, other program modules, and program data. These application programs, program modules, and program data are used to implement the functionality described herein, such as the method 300 described above.

In some embodiments, the medical device 104 includes input devices to enable a user to provide inputs to the medical device 104. Examples of input devices include a keyboard, a pointer input device, a microphone, and a touch sensitive display. Other embodiments include other input devices. These input devices can be connected by any number of input/output interfaces, such as a parallel port, serial port, game port, or a universal serial bus. Wireless communication is possible as well, and includes infrared, Bluetooth wireless technology, 802.11a/b/g/n/ac/ad, cellular, or other radio frequency communication systems in some possible embodiments. Wireless communication allows other devices, such as a smart phone to act as the input and/or output device for medical device 104.

In this example embodiment, a touch sensitive display device is also provided. The touch sensitive display device includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the medical device 104 can include various other peripheral devices (not shown), such as speakers or a printer.

When used in a local area networking environment or a wide area networking environment (such as the Internet), the medical device 104 is typically connected to the network through a network interface. Other possible embodiments use other communication devices. For example, some embodiments of the medical device 104 include an Ethernet network interface, or a modem for communicating across the network.

The medical device 104 typically includes at least some form of computer-readable media. Computer readable media includes any available media that can be accessed by the medical device 104. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the medical device 104. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A system for determining a hydration level of an individual, the system comprising:
    a mechanism configured to apply mechanical pressure to a digit of the individual;
    a light detector configured to sense a light from the digit; and
    a controller programmed to perform functions comprising:
        send a first signal to the mechanism to apply the mechanical pressure to the digit;
        send a second signal to the mechanism to release the mechanical pressure on the digit;
        determine a capillary refill time based upon a third signal from the light detector indicating an amount of time for capillaries of the individual to refill with blood;
        access an algorithm that is trained on clinically reviewed capillary refill waveforms, with each of the clinically reviewed capillary refill waveforms having undergone multiple clinical reviews by clinicians;
        use the algorithm to estimate a percentage of dehydration based upon dehydrated and rehydrated weights; and
        calculate a percentage of dehydration of the individual by application of the algorithm, with inputs to the algorithm including the capillary refill time and one or more additional parameters.

2. The system of claim 1, further comprising
    at least one sensor configured to sense a presence of the digit; and
    a light source configured to direct the light into the digit.

3. The system of claim 2, wherein the controller is further programmed to perform functions comprising:
    receive a signal from the at least one sensor indicating the presence of the digit; and
    determine when to release the mechanical pressure based upon a desired pressure.

4. The system of claim 1, wherein the digit is a finger or toe of the individual.

5. The system of claim 1, wherein the one or more additional parameters includes a temperature of the digit.

6. The system of claim 1, wherein the one or more additional parameters includes a pulse rate of the individual.

7. The system of claim 1, further comprising a light-emitting diode positioned to emit the light into the digit.

8. The system of claim 1, wherein the light detector is configured to sense an intensity of the light that is transmitted through the digit or the light that is reflected from the digit.

9. The system of claim 1, further comprising a display configured to show a score associated with the hydration level of the individual.

10. The system of claim 1, wherein the system is programmed to provide an alert based upon the hydration level of the individual.

11. A system for determining a hydration level of an individual, the system comprising:
    a mechanism configured to apply mechanical pressure to a digit of the individual;
    at least one sensor configured to sense a presence of the digit;
    a light source configured to direct light into the digit;
    a light detector configured to sense the light from the digit;
    a temperature detector configured to sense a temperature of the digit; and
    a controller programmed to perform functions comprising:
        send a first signal to the mechanism to apply the mechanical pressure to the digit;
        send a second signal to the mechanism to release the mechanical pressure on the digit;
        determine a capillary refill time based upon a third signal from the light detector indicating an amount of time for capillaries of the individual to refill with blood;
        access an algorithm that is trained on clinically reviewed capillary refill waveforms, with each of the clinically reviewed capillary refill waveforms having undergone multiple clinical reviews by clinicians;
use the algorithm to estimate a percentage of dehydration based upon dehydrated and rehydrated weights; and
calculate a percentage of dehydration of the individual by application of algorithm, with inputs to the algorithm including the capillary refill time and one or more additional parameters, the one or more additional parameters including the temperature of the digit.

12. The system of claim 11, wherein the controller is further programmed to perform functions comprising:
receive a signal from the at least one sensor indicating a presence of the digit; and
determine when to release the mechanical pressure based upon a desired pressure.

13. The system of claim 11, wherein the light detector is configured to sense an intensity of the light that is transmitted through the digit or the light that is reflected from the digit.

14. The system of claim 11, further comprising a display configured to who a score associated with the hydration level of the individual.

15. The system of claim 11, wherein the system is programmed to provide an alert based upon the hydration level of the individual.

16. A method for determining a hydration level of an individual, the method comprising:
causing a mechanical pressure to be applied to a digit of the individual;
injecting a light into the digit of the individual;
detecting the light from the digit of the individual;
determining a capillary refill time based upon the detecting of the light;
accessing an algorithm that is trained on clinically reviewed capillary refill waveforms, with each of the clinically reviewed capillary refill waveforms having undergone multiple clinical reviews by clinicians;
using the algorithm to estimate a percentage of dehydration based upon dehydrated and rehydrated weights; and
calculating a percentage of dehydration of the individual by applying the algorithm, with inputs to the algorithm including the capillary refill time and one or more additional parameters.

17. The method of claim 16, further comprising:
determining a presence of the digit; and
determining when to release the mechanical pressure based upon a desired pressure.

18. The method of claim 16, further comprising:
measuring a temperature of the digit; and
using the temperature as one of the one or more additional parameters.

19. The method of claim 16, further comprising displaying a score associated with the hydration level of the individual.

20. The method of claim 16, further comprising providing an alert based upon the hydration level of the individual.

* * * * *